United States Patent [19]

Shoesmith, deceased

[11] Patent Number: Plant 5,934

[45] Date of Patent: Apr. 7, 1987

[54] CHRYSANTHEMUM PLANT NAMED FRISKY

[75] Inventor: Leonard H. Shoesmith, deceased, late of Westfield, England, by May V. Shoesmith, executrix

[73] Assignee: Ball Pan Am Plant Co., Parrish, Fla.

[21] Appl. No.: 712,693

[22] Filed: Mar. 18, 1985

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Chrysanthemum named Frisky having a dwarf habit, late eight to early nine week response, anemone flower form, white ray florets with yellow disc florets or cushion, and an ability to be grown year around in 9 cm. pots with little growth regulation.

1 Drawing Figure

The present invention comprises a new and distinct cultivar of *Chrysanthemum morifolium,* Ramat., hereinafter referred to by the cultivar name Frisky.

Frisky is a product of a planned breeding program which had the objective of creating new Chrysanthemum cultivars with eight (8) week response, anemone flower form, white ray floret color with a yellow cushion, and a dwarf habit suitable for year around growing in 9 cm. pots. Such traits in combination were not present in previously available commercial cultivars.

Frisky was originated from a hybridization made by Leonard H. Shoesmith controlled breeding program in Westfield, Woking, England in 1976. The male and female parents are unknown at this time. Frisky was discovered and selected as one flowering plant within the progeny of the parentage by applicant in November, 1977 in a controlled environment in West Chicago, Ill., and given the code name F7-410-WS.

The first act of asexual reproduction of Frisky was accomplished when vegetative cuttings were taken from the initial selection in February, 1978 in a controlled environment in West Chicago, Ill. by a technician working under formulations established and supervised by Leonard H. Shoesmith. Horticultural examination of selected units initiated in March, 1978 has demonstrated that the combination of characteristics as herein disclosed for Frisky are firmly fixed and are retained through successive generations of asexual reproduction.

Frisky has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Frisky, which in combination distinguish this Chrysanthemum as a new and distinct cultivar:

1. Dwarf habit.
2. Late eight (8) to early nine (9) week response.
3. Anemone flower form.
4. White ray florets.
5. Yellow disc florets or cushion.

6. Ability to be grown year around in 9 cm. pots in most areas, and requiring few B-9 treatments.

Of the many commercial cultivars known to the present inventor, the most similar in comparison to Frisky is the cultivar Frosty, disclosed in U.S. Plant patent application Ser. No. 488,771, filed Apr. 26, 1983. In comparison to Frosty, Frisky has smaller leaves, is shorter (more compact), has smaller flowers, has a deeper and more intense yellow cushion, and is easier to grow in 9 cm. pots in a year around program. The flower form of Frisky is similar to that same characteristic of Frosty.

The accompanying photographic drawing of Frisky comprises a black and white photograph, with the disc florets or cushion of one flower containing the true flower color of the disc florets.

In the following description color references are made to The Royal Horticultural Society Colour Chart. The color values were determined at approximately 11:00 a.m. on Jan. 17, 1985 under natural and fluorescent light at Bradenton, Fla.

Classification:

*Botanical.*—*Chrysanthemum morifolium,* Ramat., cv. Frisky.

*Commercial.*—Anemone CBR, four (4) inch pot.

INFLORESCENCE

A. Capitulum:

*Form.*—Flat.

*Type.*—Anemone.

*Diameter across face.*—2–3 cm.

B. Corolla of ray florets:

*Color (general tonality from a distance of three meters).*—White.

*Color (under surface).*—155B-C.

*Color (top surface).*—155B.

C. Corolla of disc florets:

*Color (mature cushion).*—9A.

*Color (immature).*—Lime green, approximately 154A-B.

D. Reproductive organs:

*Androecium.*—Present in disc florets only; numerous.

*Gynoecium.*—Present in both ray and disc florets; numerous.

PLANT

A. General appearance:

*Height.*—15–25 cm. above edge of pot when properly grown in 9 cm. pot.

B. Foliage:

*Color (under surface).*—147 B.

*Color (top surface).*—147 A.

*Shape.*—Ovate and deeply lobed.

It is claimed:

1. A new and distinct cultivar of Chrysanthemum named Frisky, as described and illustrated, and particularly characterized by its dwarf habit; late eight to early nine week response; anemone flower form; white ray florets with yellow disc florets or cushion, and by its ability to be grown year around in 9 cm. pots with little growth regulation.

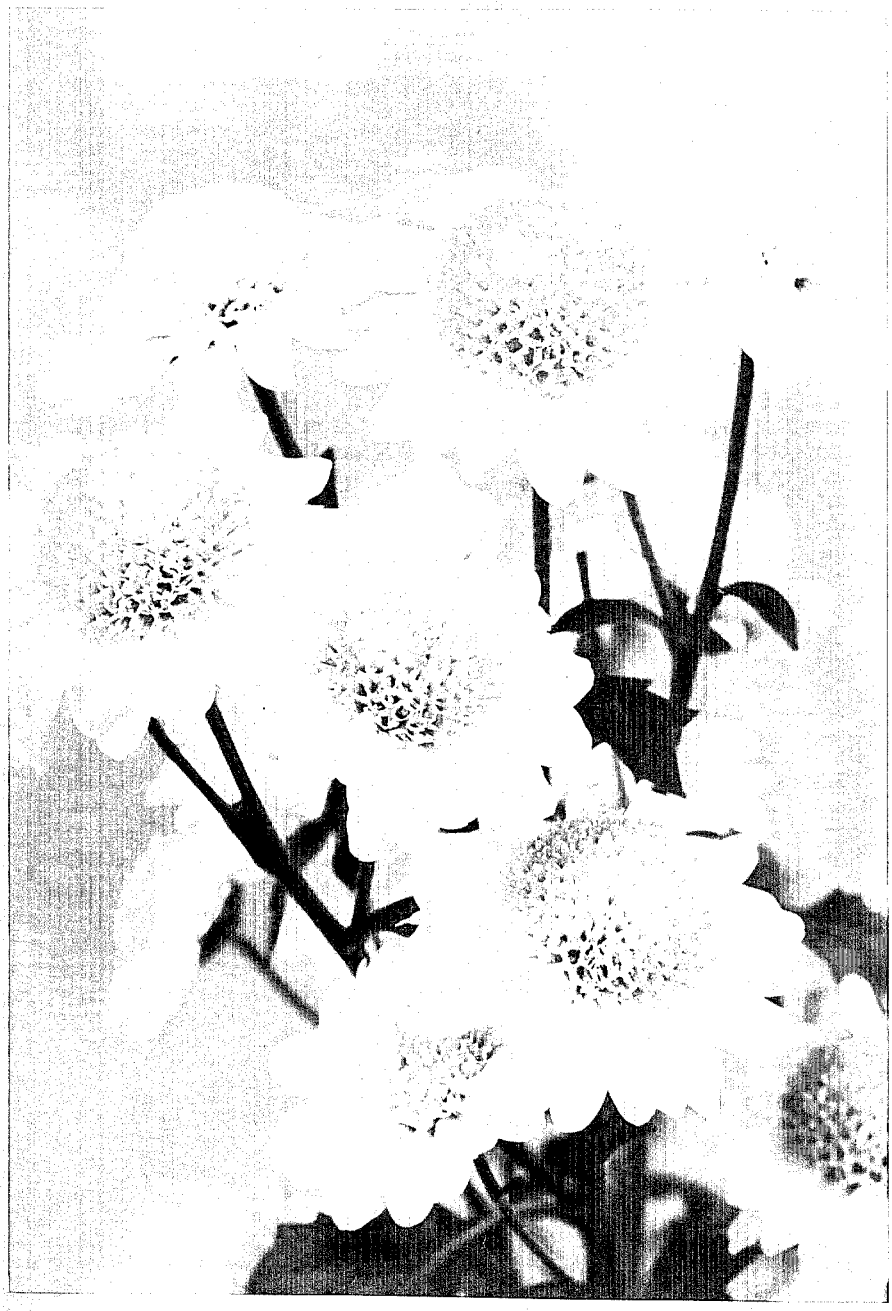

* * * * *